United States Patent
Brugger et al.

(10) Patent No.: US 6,585,681 B2
(45) Date of Patent: Jul. 1, 2003

(54) METHODS AND APPARATUS FOR PERFORMING FLOW-THROUGH PERITONEAL DIALYSIS

(75) Inventors: James Brugger, Newburyport, MA (US); Jeffrey Burbank, Boxford, MA (US); Charles Finch, Clinton, MS (US); Hendrik Kuiper, Edwards, MS (US)

(73) Assignee: Vasca, Inc., Tewksbury, MA (US)

( * ) Notice: Subject to any disclaimer, the term of this patent is extended or adjusted under 35 U.S.C. 154(b) by 0 days.

(21) Appl. No.: 09/823,736

(22) Filed: Mar. 30, 2001

(65) Prior Publication Data
US 2001/0014793 A1 Aug. 16, 2001

Related U.S. Application Data

(62) Division of application No. 09/166,341, filed on Oct. 5, 1998, now Pat. No. 6,245,039.

(51) Int. Cl.[7] ............... A61M 1/00; A61M 31/00
(52) U.S. Cl. ........................... 604/29; 604/502
(58) Field of Search ............... 604/27–30, 35, 604/93, 175, 257, 500, 502, 511, 514, 284

(56) References Cited

U.S. PATENT DOCUMENTS

| | | | |
|---|---|---|---|
| 3,707,967 A | 1/1973 | Kitrilakis et al. |
| 4,184,497 A | 1/1980 | Kolff et al. |
| 4,239,041 A | 12/1980 | Popovich et al. |
| 4,306,976 A | 12/1981 | Bazzato |
| 4,351,333 A | 9/1982 | Lazarus et al. |
| 4,381,003 A | 4/1983 | Bouncristiani |
| 4,396,382 A | 8/1983 | Goldhaber |
| 4,490,137 A | 12/1984 | Moukheiibir |
| 4,496,349 A | 1/1985 | Cosentino |
| 4,586,920 A | 5/1986 | Peabody |
| 4,832,054 A | 5/1989 | Bark |
| 5,037,385 A | 8/1991 | O'Byrne |
| 5,250,041 A | 10/1993 | Folden et al. |
| 5,254,084 A | 10/1993 | Geary |
| 5,322,519 A | 6/1994 | Ash |
| 5,334,139 A | 8/1994 | Jeppsson et al. |
| 5,338,293 A | 8/1994 | Jeppsson et al. |
| 5,421,814 A | 6/1995 | Geary |
| 5,423,768 A | 6/1995 | Folden et al. |

Primary Examiner—Sharon Kennedy
(74) Attorney, Agent, or Firm—Townsend and Townsend and Crew LLP

(57) ABSTRACT

Methods, apparatus, and kits are provided for performing peritoneal dialysis. In a first aspect, subcutaneous and transcutaneous systems are described for performing continuously cycling peritoneal dialysis. In a second aspect, fully implanted systems are described for performing flow-through peritoneal dialysis.

17 Claims, 9 Drawing Sheets

METHODS AND APPARATUS FOR PERFORMING FLOW-THROUGH PERITONEAL DIALYSIS

CROSS-REFERENCES TO RELATED APPLICATIONS

The present invention is a division of application no. 09/166,341 filed Oct. 5, 1998, now U.S. Pat. No. 6,245,039, issued on Jun. 12, 2001, the full disclosure of which is incorporated herein by reference.

BACKGROUND OF THE INVENTION

1. Field of the Invention

The present invention is generally related to medical methods, apparatus, and kits. More particularly, the present invention is related to methods, systems, and kits for performing discontinuous flow-through peritoneal dialysis.

Patients afflicted with end stage renal disease where kidney transplantation is unavailable may be treated by hemodialysis or peritoneal dialysis to remove toxic products from the patient's blood. Both techniques operate by the principles of diffusion across semipermeable membranes. In the case of peritoneal dialysis, the membrane that is used is the patient's peritoneal membrane.

Peritoneal Dialysis (PD) periodically infuses sterile aqueous solution into the peritoneal cavity. This solution is called peritoneal dialysis solution, or dialysate. Diffusion and osmosis exchanges take place between the solution and the bloodstream across the natural body membranes. These exchanges remove the waste products that the kidneys normally excrete. The waste products typically consist of solutes like sodium and chloride ions, and the other compounds normally excreted through the kidneys like urea, creatinine, and water. The diffusion of water across the peritoneal membrane during dialysis is called ultrafiltration. Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During CAPD, the patient drains spent peritoneal dialysis solution from his/her peritoneal cavity. The patient then infuses fresh peritoneal dialysis solution onto his/her peritoneal cavity. This drain and fill procedure usually takes about one hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

The APD sequence typically last for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle. During the fill phase, the cycler transfers a predetermined volume of fresh, warmed dialysate into the peritoneal cavity of the patient. The dialysate remains (or "dwells") within the peritoneal cavity for a time. This is called the dwell phase. During the drain phase, the cycler removes the spent dialysate from the peritoneal cavity. The number of fill/dwell/drain cycles that are required during a given APD session depends upon the total volume of dialysate prescribed for the patient's APD regime.

APD can be and is practiced in different ways. Continuous Cycling Peritoneal Dialysis (CCPD) is one commonly used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 6 fill/dwell/drain cycles to achieve a prescribed therapy volume. After the last prescribed fill/dwell/drain cycle in CCPD, the cycler infuses a final fill volume. The final fill volume dwells in the patient through the day. It is drained at the outset of the next CCPD session in the evening. The final fill volume can contain a different concentration of dextrose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home. Like CCPD, IPD involves a series of fill/dwell/drain cycles. The cycles in IPD are typically closer in time than in CCPD. In addition, unlike CCPD, IPD does not include a final fill phase. In IPD, the patient's peritoneal cavity is left free of dialysate (or "dry") in between APD therapy sessions.

Tidal peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse then drain a replacement volume on top of the base volume, except for the last drain phase. The last drain phase removes all dialysate from the peritoneal cavity. There is a variation of TPD that includes cycles during which the patient is completely drained and infused with a new full base volume of dialysis. TPD can include a final fill cycle, like CCPD. Alternatively, TPD can avoid the final cycle, like IPD.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

For these reasons, it would be desirable to provide improved methods, apparatus, and kits for performing peritoneal dialysis. In particular, it would be desirable to perform flow-through dialysis without the need to employ a pair of transcutaneously implanted catheters or in some cases even a single transcutaneously implanted catheter. Alternatively, it would be desirable to perform flow-through tidal peritoneal dialysis in combination with certain advantageous aspects of flow-through dialysis, while preferably retaining the benefits of requiring only a single access site, and more preferably relying on a single percutaneous access location. Such methods, apparatus, and kits should be readily adaptable for home use and minimize the risk of infection in both the home and out-of-the-home environments. At least some of these advantages will be met by the invention described hereinafter.

2. Description of the Background Art

Conventional peritoneal dialysis tubing sets and components are described in U.S. Pat. Nos. 4,306,976; 4,396,382;

5,250,041; 5,334,139; 5,338,293; and 5,423,768. U.S. Pat. No. 4,184,497 describes an implantable catheter having an enlarged hollow portion which can be punctured to receive a sterile access needle. U.S. Pat. No. 4,496,349 describes a septum-type transcutaneous access port. Co-pending application Ser. No. 08/896,791, filed on Jul. 18, 1997, and assigned to the assignee of the present application, describes a dialysis tubing set which could be used in the methods and systems of the present invention. The full disclosures of this application and all listed U.S. patents are incorporated herein by reference.

BRIEF SUMMARY OF THE INVENTION

The present invention provides improved methods, apparatus, and kits for performing peritoneal dialysis in both home and out-of-the-home environments. In particular, improved methods, apparatus, and kits according to the present invention for performing continuously cycling dialysis protocols allow for cycling between spaced-apart locations in the peritoneum while needing only a single percutaneous or transcutaneous access location through the patient's skin. By relying on spaced-apart infusion and drain locations within the peritoneum, at least some of the benefits associated with flow-through dialysis may be achieved in a continuously cycling protocol using only a single access location. Alternatively, improved methods, apparatus, and kits for performing flow-through dialysis according to the present invention rely on separate percutaneous access to two subcutaneously implanted ports attached to separate infusion and drain catheters, respectively. The implanted ports are percutaneously accessed using needles or other access tubes. By eliminating the need to employ transcutaneous catheters, the risk of infection to the patient is greatly reduced.

A specific method for performing continuously cycling peritoneal dialysis according to the present invention comprises infusing dialysate to an implanted infusion catheter through an access location and draining dialysate from an implanted drain catheter through the same access location. Usually, after an initial volume of dialysate has been infused into the peritoneum, the infusing and draining steps will be performed in an alternating or cycling manner. By relying on spaced-apart infusion catheter and drain catheter locations, however, the flow will be maintained generally in the same direction at all times, i.e., from the infusion catheter to the drain catheter. In this way, the benefits of flow-through dialysis can be achieved without having to employ a pair of transcutaneously implanted catheters.

In a preferred aspect of the continuously cycling method, the infusing step comprises percutaneously introducing an access tube, typically a needle, cannula/stylet, or other conventional coupling element to an implanted port attached to the infusion catheter. The dialysate may then be introduced at a positive pressure through the access tube and into the peritoneum. The positive pressure may be established by gravity flow or alternatively by using an external pump system. The draining step preferably comprises opening an access tube or similar coupling element which has been introduced to the same access port. Usually, the access tube for both infusion and draining will be the same, but it would also be possible to exchange different access tubes to the same implanted access port. Drainage will usually occur in response to the pressure of dialysate which has built up in the peritoneum, but in some instances it may be desirable to apply a negative pressure to the access tube to help draw the dialysate out.

While it is generally preferred to percutaneously introduce the access tube to an implanted port, as described above, the present invention may also be performed using a single transcutaneously implanted catheter which is subcutaneously attached to both the infusion catheter and the drain catheter. An external hub, connector, or other element of the transcutaneous catheter can then be attached to a suitable system for both introducing and withdrawing dialysate through the catheter and alternatively into and from the infusion and drain catheters, respectively.

These methods rely on the ability to selectively direct fresh dialysate to the infusion catheter and withdraw spent dialysate from the drain catheter, with little or no mixing between the fresh and spent dialysate streams. In a first exemplary embodiment, such selective flow is achieved through a single implanted port which is subcutaneously attached to a single implanted catheter having an infusion arm and a drain arm. Each arm of the catheter is provided with a one-way flow valve structure which permits the fresh dialysate to flow into the infusion arm and the spent dialysate to flow from the drain arm. By then infusing and draining dialysate into and from the implanted catheter at successive times, the desired uni-directional flow through the peritoneum is achieved with minimum mixing of the two dialysate streams. Alternatively, a flow directing mechanism could be provided within the implanted port and/or in a separate valve structure so that dialysate being introduced into the port would flow only to the infusion catheter while spent dialysate being drained from the peritoneum would flow only outwardly through the access tube and not back flow into the infusion catheter.

This method can be performed using a transcutaneously implanted catheter, where the catheter has a bi-directional flow segment, an infusion arm, and a drain arm, where the bi-directional flow segment is adapted for transcutaneous implantation. A flow control structure, such as a pair of one-way valves as described above, may then be provided within the catheter to assure that dialysate being introduced through the bi-directional flow segment will flow only to the infusion arm and not back flow into the bi-directional flow segment, while spent dialysate being drawn from the drain arm will flow only into the bi-directional flow segment, and not back flow.

When using a transcutaneously implanted catheter, as just described, the continuously cycling methods may be performed by maintaining separate, isolated flow lumens within the bi-directional flow segment, where a first of the lumens is attached to the infusion arm and a second of the lumens is attached to the drain arm. Using such catheters, access to the infusion arm and drain arm may be maintained through a single transcutaneous location, and either flow-through dialysis or continuous cycling dialysis may be performed. For flow-through dialysis, the flow may be continuously introduced through the first isolated lumen and into the infusion arm and simultaneously withdrawn through the drain arm and second isolated lumen.

Kits for accessing an implanted port of a continuously cycling peritoneal dialysis system comprise an access catheter having an access tube at a distal end thereof. The access tube may be a needle or any of the other devices described above which permit temporary access to an implanted port attached to an infusion catheter and a drain catheter. The kits will include instructions for use according to any of the methods described above. In addition, the kits will usually include packaging, such as a pouch, tray, box, tube, or the like, where the kits components are maintained sterilely within the packaging. Other kit components include reagent(s) necessary to prepare the dialysate fluid, tubes, tube connectors, and the like.

A kit for accessing a transcutaneously implanted continuously cycling peritoneal dialysis system includes an access catheter having an access hub or other connector at its distal end. The access hub is adapted for connecting to the proximal end of a transcutaneously implanted dialysis catheter having an infusion arm and a drain arm. The kit will further comprise instructions for use according to any of the methods set forth above, and will usually include packaging as described above. Other kit components may also be maintained within the packaging, typically in a sterile manner.

A preferred peritoneal dialysis catheter according to the present invention comprises a bi-directional flow segment, an infusion arm, and a drain arm. The bi-directional flow segment has a proximal end adapted to receive and discharge dialysate in a distal end. The infusion arm is connected to receive dialysate from the bi-directional flow segment, where the infusion arm inhibits back flow from the arm to the bi-directional flow segment. A drain arm is connected to discharge dialysate to the bi-directional flow segment, where the drain arm inhibits back flow from the bi-directional flow segment to the drain arm. Preferably, the bi-directional flow segment is adapted for connection to an implantable port, but may also be adapted for transcutaneous implantation. Typically, in the latter case, the bi-directional flow segment will comprise at least one circumscribing cuff to inhibit the transmission of fluids along the outside surface of the catheter. Often, at least two such cuffs will be provided. The inclusion of such cuffs is well known and described in the art for transcutaneously implanted catheters. For both the fully implantable and transcutaneous catheters, the infusion and drain arms will typically include valve structures which establish the desired flow patterns, i.e., dialysate flowing in from the bi-directional flow segment will flow only into the infusion arm while spent dialysate being drawn from the drain arm will flow only or primarily out through the bi-directional flow segment.

Such catheter structures may be fabricated from conventional materials, such as silicone rubber, polyurethane, and the like, and may be fabricated as a single, continuous structure or as separate components which are later joined together using fittings, thermal welding, adhesives, or the like.

The peritoneal dialysis catheters just described may be combined into systems, typically including an implantable port adapted to be connected to the proximal end of the bi-directional flow segment of the catheter. Such implantable ports will preferably be valved port structures, such as described in co-pending application Ser. No. 08/942,990, filed on Oct. 2, 1997, now U.S. Pat. No. 6,007,516, issued Dec. 28, 1999, assigned to the assignee of the present application, the full disclosure of which is incorporated herein by reference. Other suitable valved port structures are described in the patent literature. The systems may also include implantable ports which comprise a needle-penetrable membrane. Particularly preferred are valved implantable ports having a flow capacity of at least 50 ml/min, more preferably at least 200 ml/min, and still more preferably at least 300 ml/min, or above.

The present invention further provides methods for implanting a peritoneal dialysis system which includes an infusion catheter, a drain catheter, and a single access port. The method comprises subcutaneously implanting the infusion catheter in the peritoneum of a patient and subcutaneously implanting a drain catheter in the peritoneum at a location spaced-apart from that of the infusion catheter. The port is also subcutaneously implanted and is connected to both the infusion catheter and the drain catheter. Preferably, structure for directing flow of fresh dialysate from the port to the infusion catheter and spent dialysate from the drain catheter to the port will be provided, usually comprising one-way flow valves as discussed above.

The present invention still further provides kits for implanting peritoneal dialysis catheters. The kits comprise an infusion catheter, a drain catheter, and instructions for use for implanting the catheters, usually with an implantable port, generally as discussed above. The implantable port may be part of the same kit, or may be provided separately.

The present invention also provides methods for transcutaneously implanting catheters for performing continuously cycling peritoneal dialysis. Infusion and drain catheters are implanted in the peritoneum of the patient in a spaced-apart manner, generally as described above. A single bi-directional flow catheter which is connected to both the infusion catheter and the drain catheter is transcutaneously implanted to provide an infusion path into the infusion catheter and a drain path from the drain catheter. Usually, the infusion catheter, drain catheter, and bi-directional flow catheter will comprise a single, preformed catheter unit or assembly. Alternatively, the components may be separate and connected together either immediately prior to implantation or after implantation.

Kits for implanting such continuously cycling peritoneal dialysis systems comprise the infusion catheter, the drain catheter, the bi-directional flow catheter, and instructions for use according to the method just set forth.

Methods according to the present invention for performing flow-through dialysis comprise percutaneously introducing a first access tube to an implanted port attached to an implanted infusion catheter. A second access tube is percutaneously introduced to an implanted port attached to an implanted drain catheter. Dialysate is then infused through the first access catheter to the implanted catheter and into the patient's peritoneum. Such infusion may be effected by gravity flow, pumping, and the like, and will usually be performed for a time sufficient to introduce an initial volume of the dialysate within the ranges set forth above. After at least some dialysate is introduced, and preferably at least the desired initial volume, dialysate flow is initiated through the drain catheter and second access tube from the peritoneum. Usually, the fluid pressure in the peritoneum is sufficient to maintain the desired drainage rate, but it would be possible to apply a negative pressure to the second access tube if necessary for any reason. After the withdrawal of spent dialysate is commenced, the fresh dialysate will normally continue to be introduced at generally the same rate at which it is being withdrawn, typically in the range from 50 ml/min to 300 ml/min, usually from 100 ml/min to 200 ml/min. Such flow-through dialysis will then be continued for from one hour to twelve hours, usually from four hours to nine hours. The treatment protocol can then be terminated by stopping the infusion of fresh dialysate while continuing to withdraw the spent dialysate until it is substantially completely removed.

Kits for accessing such implanted flow-through peritoneal dialysis systems comprise an infusion access catheter and a drain access catheter, each having an access tube at a distal end thereof. The access tube is adapted to percutaneously access the associated implanted infusion port. Such kits will further comprise instructions for use according to the methods set forth above, and may still further comprise packaging, dialysate, and other components and reagents useful for performing the flow-through treatment protocol.

A peritoneal dialysis system for performing flow-through dialysis comprises an implantable infusion catheter having a proximal end adapted for connection to an implantable port and an implantable drain catheter having a proximal end adapted for connection to an implantable port. The system may optionally further comprise one, or more usually two, implantable ports for connection to the catheters. Usually, both implantable ports will comprise valve mechanisms, as generally described above. Alternatively, the ports could comprise needle-penetrable membranes to allow for access via the access tubes.

A method for implanting a flow-through peritoneal dialysis system according to the present invention comprises subcutaneously implanting an infusion catheter in the peritoneum of a patient. A drain catheter is also subcutaneously implanted in the peritoneum where the infusion and drain catheters are preferably spaced-apart, usually with the infusion catheter at the top of the peritoneal cavity and the drain catheter at the bottom of the peritoneal cavity. An infusion port is also implanted and connected to the infusion catheter. The port may be any of the types generally described above, and may be attached to the catheter either before or after implantation. Similarly, a drain port is subcutaneously implanted and connected to the drain catheter, where the drain port may be any of the types described above and may be connected to the drain catheter either before or after implantation.

Kits for implanting such flow-through peritoneal dialysis systems will include at least the infusion catheter and the drain catheter together with instructions for use according to the methods described above. Usually, the kits will further comprise the infusion port and the drain port, and may optionally further comprise other components useful for carrying out the implantation.

DESCRIPTION OF THE SPECIFIC EMBODIMENTS

Figure 1:
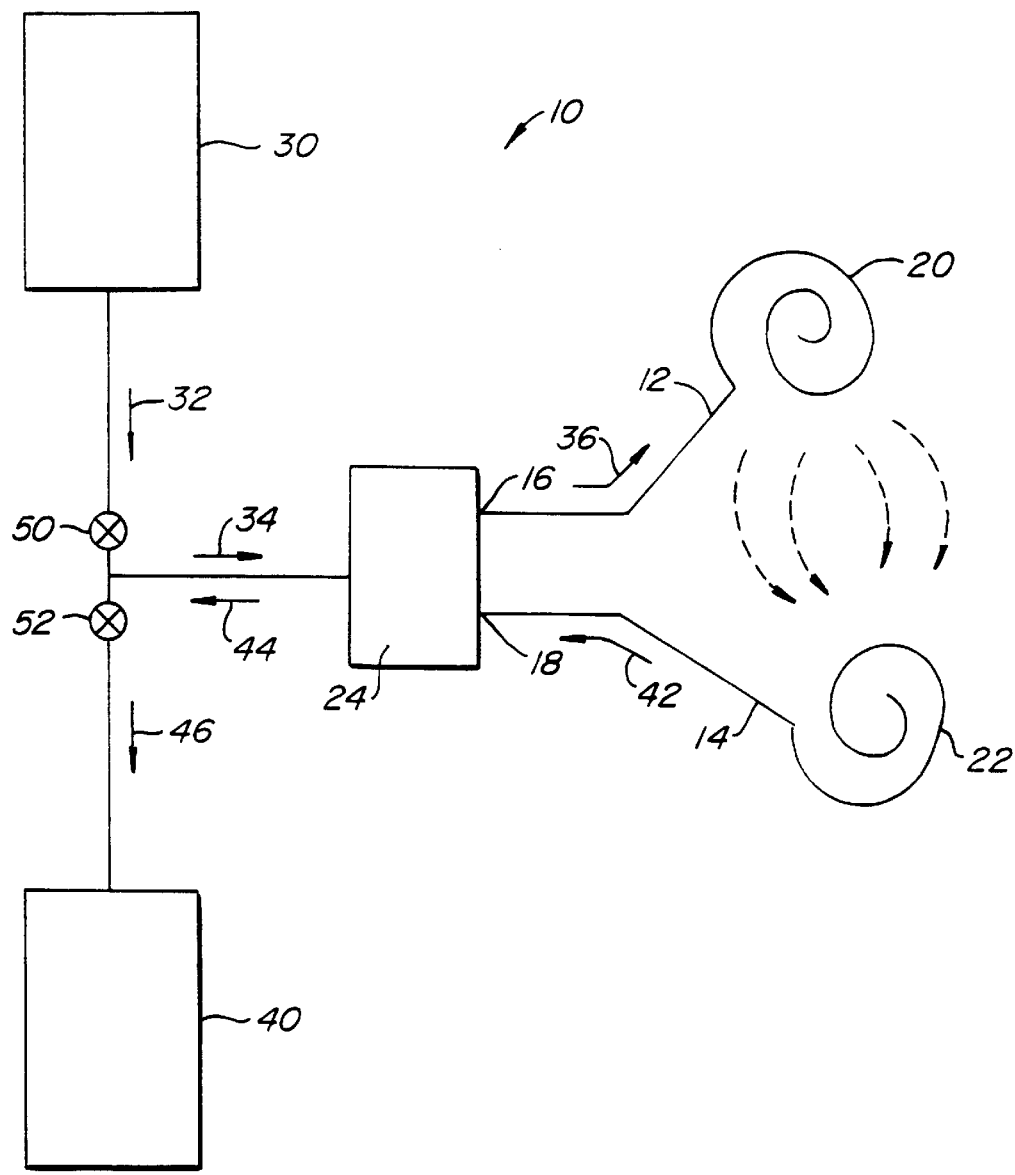
FIG. 1 is a schematic illustration of a system for performing continuously cycling peritoneal dialysis according to the present invention.

Referring now to FIG. 1, a system 10 for performing continuously cycling peritoneal dialysis according to the present invention comprises an infusion catheter 12 and a drain catheter 14. The infusion catheter 12 and drain catheter 14 comprise proximal ends 16 and 18, respectively, and distal ends 20 and 22, respectively. The distal ends 20 and 22 are configured in a manner conventional for peritoneal dialysis catheters, e.g., they may be formed in a spiral pattern and have ports or perforations formed therein to facilitate release and collection of dialysate, respectively. These aspects of the construction of catheters 12 and 14 are well described in the background patents listed and incorporated by reference herein above.

The continuously cycling peritoneal dialysis system 10 relies on both the infusion and draining dialysate through a single access location in the patient's skin. In the case of percutaneous access, the single access location will be defined by an aperture or other access target in an implanted port, as described hereinafter. In the case of transcutaneous access, the access location will be defined by a single transcutaneously positioned catheter tube. In both cases, it is necessary to connect the proximal ends 16 and 18 of the catheters 20 and 22, respectively, so that flow into and through the single access location passes into the infusion catheter 12 and that flow from the drain catheter 22 passes outwardly through the access location so that it may be collected. Additionally, it is desirable that cross-flow and/or backflow between the two catheters be minimized or eliminated. To achieve these objectives, a flow control structure 24 will be provided. In the exemplary embodiments, the flow control structure will comprise a pair of one-way valves which permit flow into the infusion catheter only and flow from the drain catheter only. The one-way valves will preferably be built into the catheters themselves, but could also be provided as part of the implantable port in the case of implantable systems. Alternatively, three-way valve mechanisms could be built into the catheters, into implantable ports, and/or be provided as part of a separate flow control structure in order to control the flow. A variety of specific mechanisms will be possible and it is necessary only that the flow be controlled so that flow from a dialysate source 30 may pass into the flow control structure 24 and be directed appropriately to the infusion catheter 12, as indicated by arrows 32, 34, and 36, while flow from the drain catheter 22 will pass into the flow control structure 24 and then be directed into a collection receptacle 40, as indicated by arrows 42, 44, and 46.

Flow from the dialysate source 30 may be effected either by gravity or by pumping. In the case of gravity flow, a valve 50 may be provided in order to control flow. In the case of actively pumped systems, the valve 50 may be replaced by a controllable pump. Similarly, flow from the flow control structure 24 to the spent dialysate receptacle 40 may be controlled by a valve 52 in the case of gravity systems. The valve 52 may be replaced by a pump in the case of actively pumped systems. Such gravity and actively pumped flow systems are well known and described in the medical and patent literature.

Figure 2:
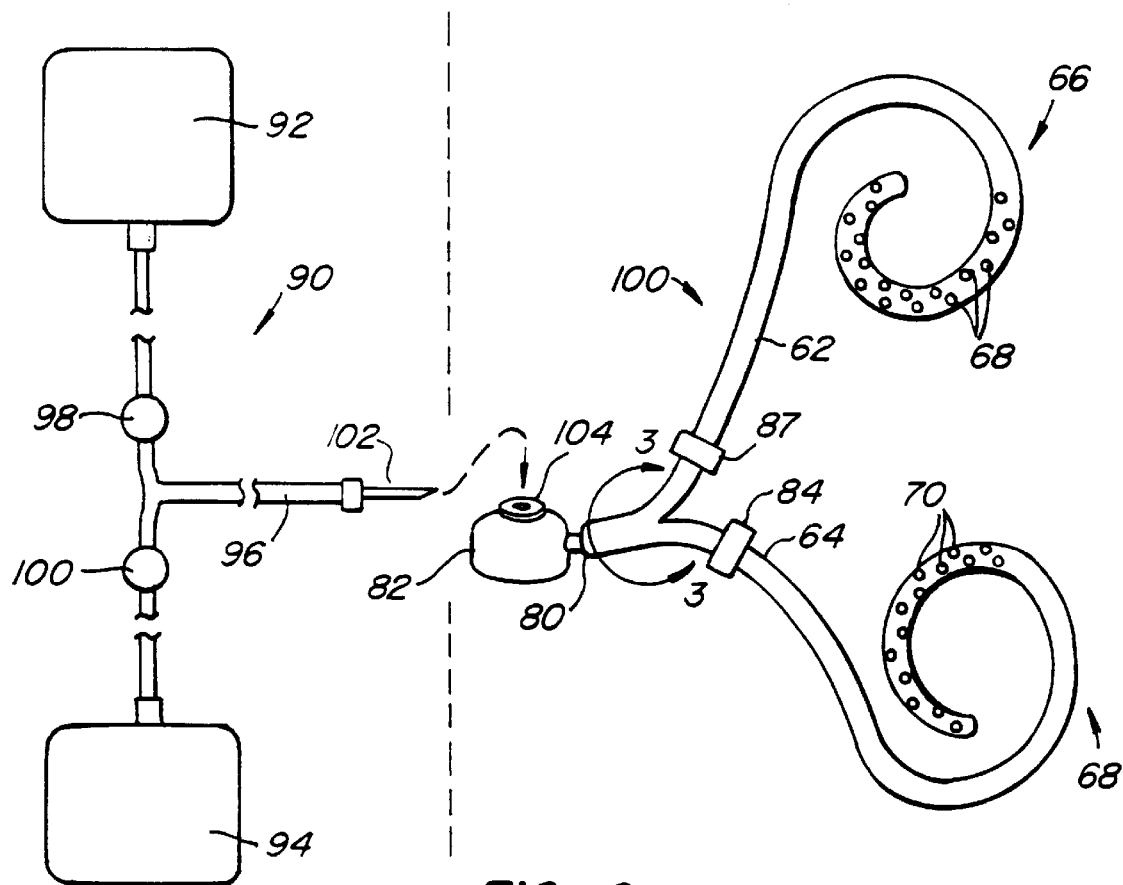
FIG. 2 illustrates an exemplary embodiment of a system comprising a subcutaneously implantable catheter, an attached port, and an access catheter assembly intended for performing continuously cycling peritoneal dialysis according to the present invention.
Figure 3:
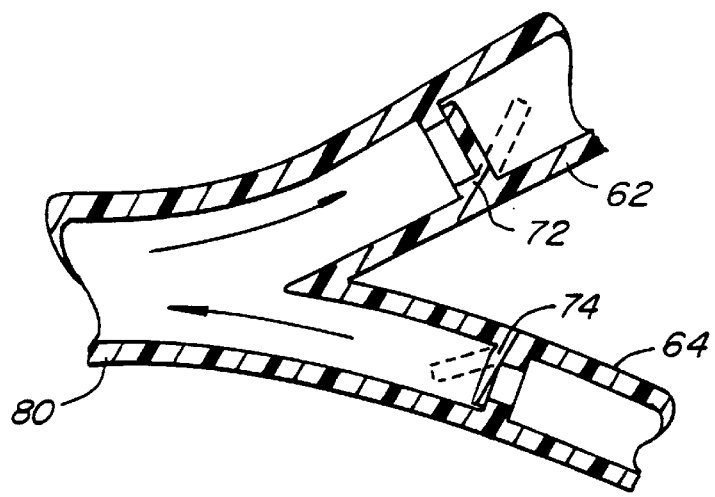
FIG. 3 is a detailed view taken along line 3—3 in FIG. 2, shown in section.
Figure 2A:
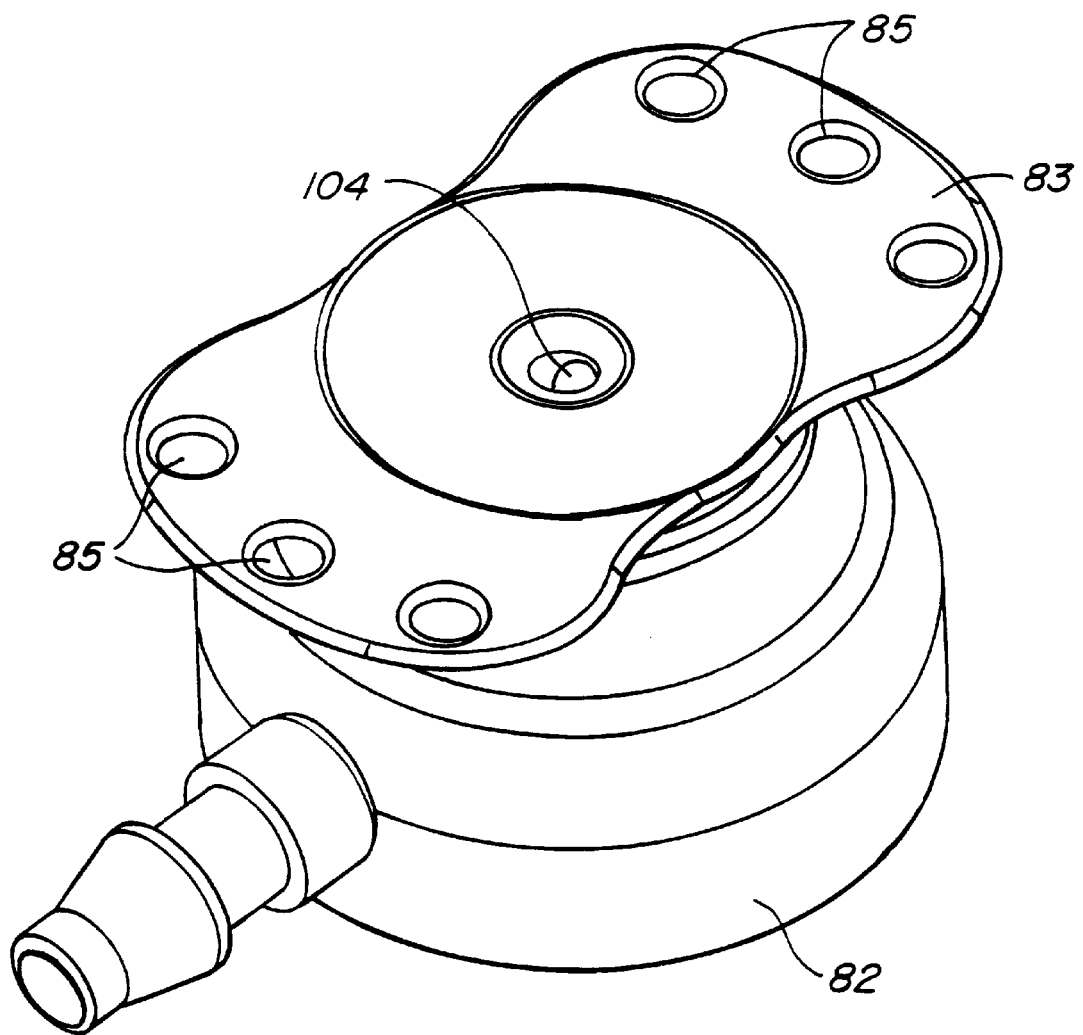
FIG. 2A illustrates an implantable port that can be used in the methods, systems, and kits of the present invention.

Referring now to FIGS. 2 and 3, a preferred system for performing continuously cycling peritoneal dialysis according to the present invention will be described. The system comprises a fully implantable catheter 60 having an infusion arm 62 and a drain arm 64. The arms 62 and 64 are tubular members having inner flow lumens, typically being composed from silicone rubber, polyurethane, or the like. The distal ends 66 and 67 are adapted for flowing dialysate into and out of the peritoneum, e.g., being formed into spiral configurations with apertures or perforations 68 and 70 formed over the spiral portions.

As best seen in FIG. 3, the proximal ends of the infusion arm 62 and drain arm 64 are joined together in a Y-junction with a one-way infusion valve 72 formed in the base of the infusion arm 62 and a one-way drain valve 74 formed in the base of the drain arm 64.

The infusion arm 62 and drain arm 64 of the catheter 60 are joined at their bases to a bi-directional flow segment 80 which has a proximal end adapted for connection to an implantable port 82. Implantable port 82 may have a wide variety of configurations, but will preferably include a needle-actuated valve, as described in U.S. Pat. No. 6,007,516, which has previously been incorporated herein by reference. The catheter 60 and port 82 may be subcutaneously implanted in the peritoneum of a patient in a generally conventional manner. Optionally, the port 82 may include a flange 83 on its upper surface, circumscribing an access aperture 104. The flange will include suture holes 85 which facilitate suturing of the port 82 to the under surface of the peritoneum of other body structure to which the port may be attached. Usually, cuffs 87 and 89 will be positioned over the proximal ends of the infusion arm 62 and the drain arm 64, respectively, to inhibit the spread of infection from the port 82 down the arms. Alternatively, a single cuff could be provided over the common tubular region of the catheter 60 nearer to the port connection.

After the catheter 60 and port 82 have been implanted, they may be accessed using a conventional peritoneal dialysis Y-set 90 which includes a bag 92 holding fresh dialysate and a bag 94 for collecting spent dialysate. The tube bags are connected together to a common access tube 96 with flow to and from the access tube controlled by valves 98 and 100, respectively. Alternatively, flow control could be provided by internal or external peristaltic or other pumps. Access to the implanted catheter 60 is provided by percutaneously introducing needle 102 or other access device so that it enters into an aperture 104 on the port 82. The needle 102 will open the valve in the port and permit both the inflow of fresh dialysate into the infusion arm 62 of catheter 60 as well as permit the collection of the outflow spent dialysate from collection arm 64. In particular, dialysate will be introduced at a positive pressure will pass through the infusion valve 72, as shown in broken line in FIG. 3. Such positive pressure will maintain the drain valve 74 closed, as shown in full line in FIG. 3. Thus, dialysate will flow through the infusion arm 62 into the patient's peritoneum, but spent dialysate will not be collected as the fresh dialysate is being introduced.

When it is desired to collect spent dialysate, flow from the dialysate source 92 will be stopped, either by closing valve 98 or stopping an associated pump. A slight negative pressure will then be drawn through the common tube 96 of the dialysate set 90, either by gravity flow into the dialysate collection receptacle 94 or by pumping. The negative pressure will cause drain valve 74 to open, as shown in broken line in FIG. 3, while keeping the infusion valve 72 firmly closed, as shown in full line in FIG. 3. The dialysate will flow through the port 92 and into the collection receptacle 94 until a desired amount of spent dialysate has been collected. The infusion and collection steps can be repeated in an alternating fashion for as long as desired. It will be appreciated that by repeating such steps, incremental flow from the infusion arm 62 to the drain arm 64 will be established.

Figure 4:
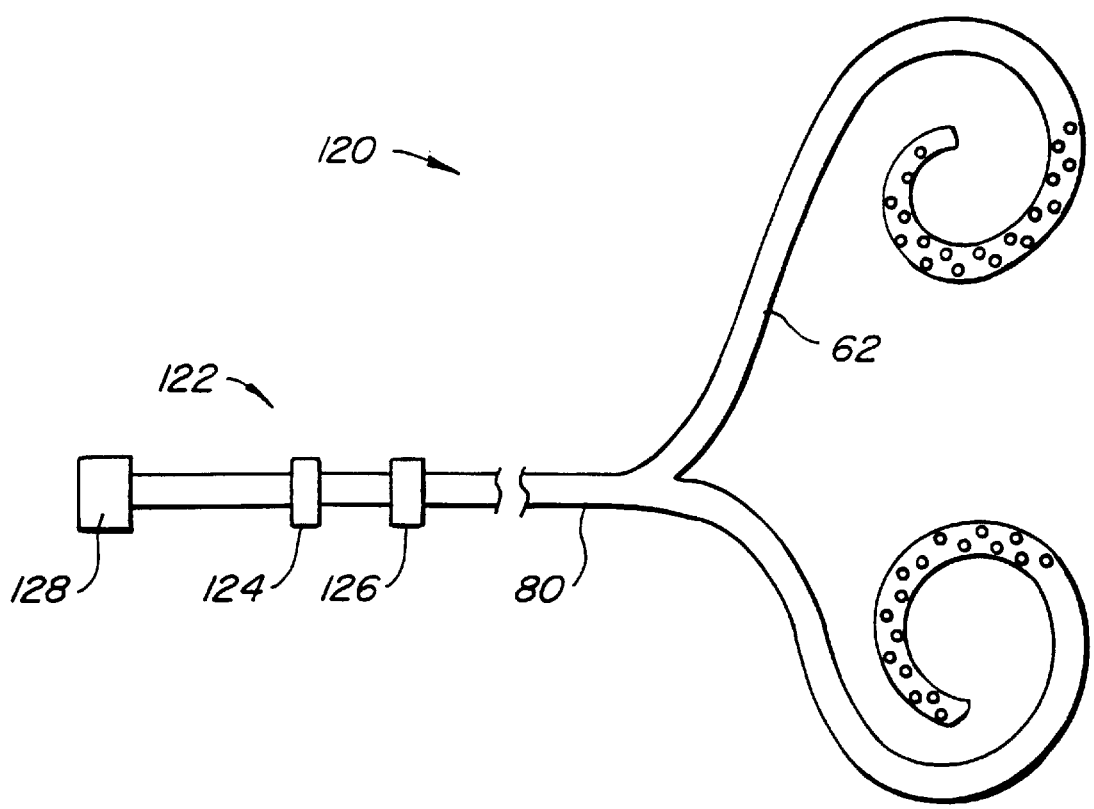
FIG. 4 illustrates transcutaneously implantable catheter suitable for performing continuously cycling peritoneal dialysis according to the present invention.

The continuously cycling peritoneal dialysis system illustrated in FIGS. 2 and 3 is intended for complete subcutaneous implantation with periodic access through a percutaneous penetration using the needle or other access tube 102. The present invention is also suitable for implementation with a transcutaneous catheter 120, as illustrated in FIG. 4.

Infusion arm 62, drain arm 64, and bi-directional flow segment 80 may all be identical to the corresponding components in catheter 60 described above. Instead of adapting the proximal end of the bi-directional flow segment for connection to an implantable port, however, proximal end 122 is adapted for transcutaneous implantation, typically including at least one, and more preferably two, cuffs 124 and 126 which help prevent transmission of infection to the distal portions of the catheter 120. A proximal hub 128 is provided for connection to an external dialysate source and collection receptacle. The hub may comprise a septum, valve, or other suitable access component. Implantation of the catheter 120 will generally be as described above, except that the proximal end of the catheter will remain disposed through an access location in the patient's skin in a manner which is conventional for transcutaneous catheters.

Figure 5:
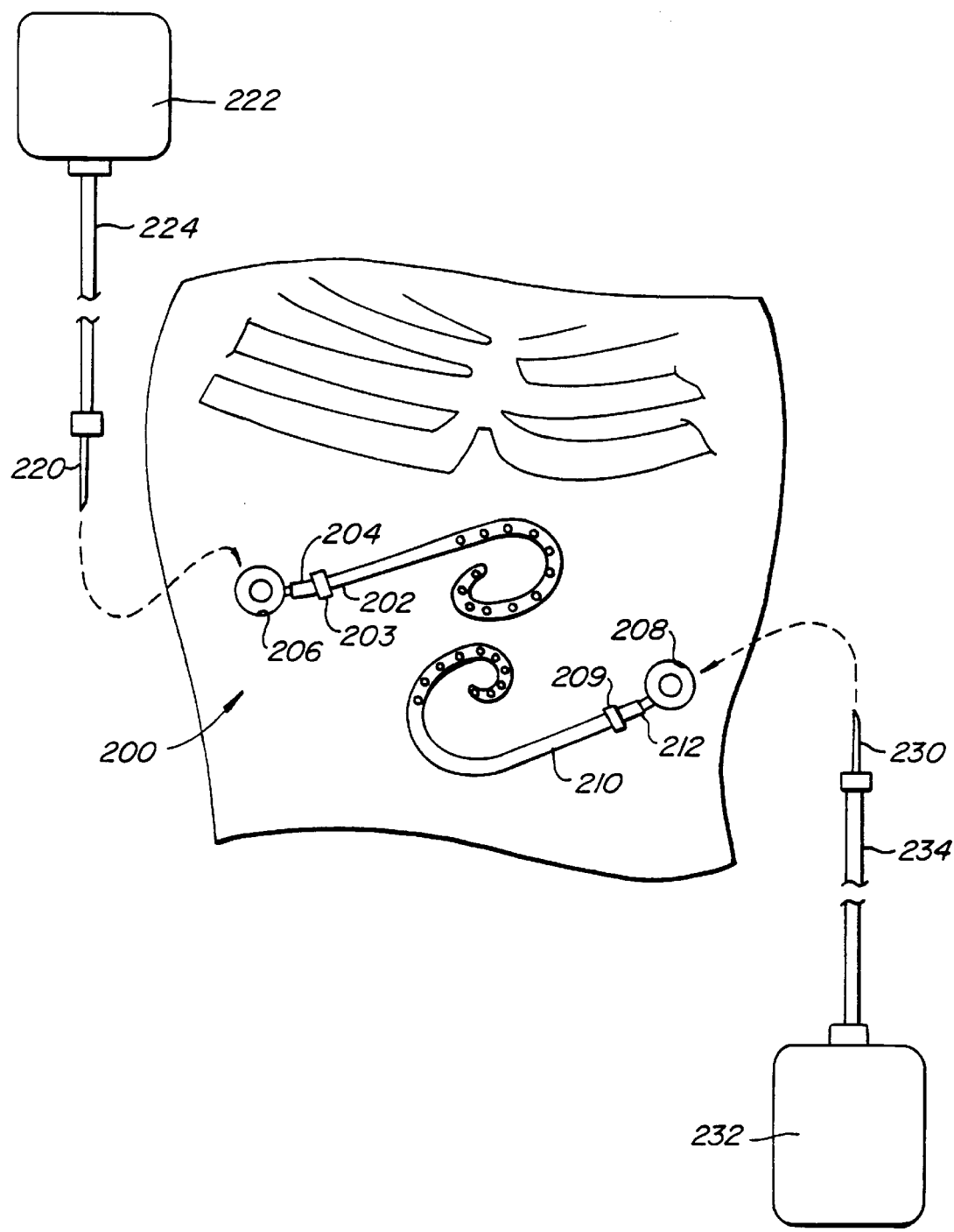
FIG. 5 illustrates a system and its use in performing flow-through peritoneal dialysis according to the present invention.

The present invention still further provides systems suitable for performing continuous flow-through peritoneal dialysis, as illustrated in FIG. 5. A system 200 comprises an infusion catheter 202 having a proximal end 204 adapted for connection to an implantable port 206. The infusion catheter may have any conventional construction for a peritoneal dialysis catheter, typically including a cuff 203 for inhibiting progress of an infection, while the port 206 will preferably be that described in co-pending application Ser. No. 08/942,990. A drain catheter 210 will typically have identical construction to the infusion catheter 202 and will have a cuff 209 and a proximal end 212 adapted for connection to an implantable port 208. Both the catheters 202 and 210 and the ports 206 and 208 will be fully implanted within the patient's peritoneum with percutaneous access being provided by separate access tubes 220 and 230, respectively. The access tube 220 will provide fresh dialysate from a bag or other receptacle 222 and will be connected through a suitable tube 224, usually having a valve, pump, or other mechanism (not shown) for controlling the flow of dialysate from the bag 222 into the port 206. Similarly, the access tube 230 will be connected to a collection bag or other receptacle 232 through a tube 234 and will typically have a valve, pump, or other mechanism (not shown) for controlling the flow of dialysate from the port 208 into the collection receptacle 232.

Since the infusion catheter 202 and drain catheter 210 are separately accessed, infusion of dialysate through the infusion catheter and collection of dialysate through the drain catheter may be performed simultaneously. Thus, a generally continuous (not cyclic) flow of dialysate from the infusion catheter 202, through the peritoneum, and to the collection catheter 210 may be maintained for relatively long periods of time, typically from one hour to twelve hours, usually from five hours to nine hours. Thus, the benefits of flow-through peritoneal dialysis may be achieved without the risks of having a pair of transcutaneously implanted catheters.

Figure 6:
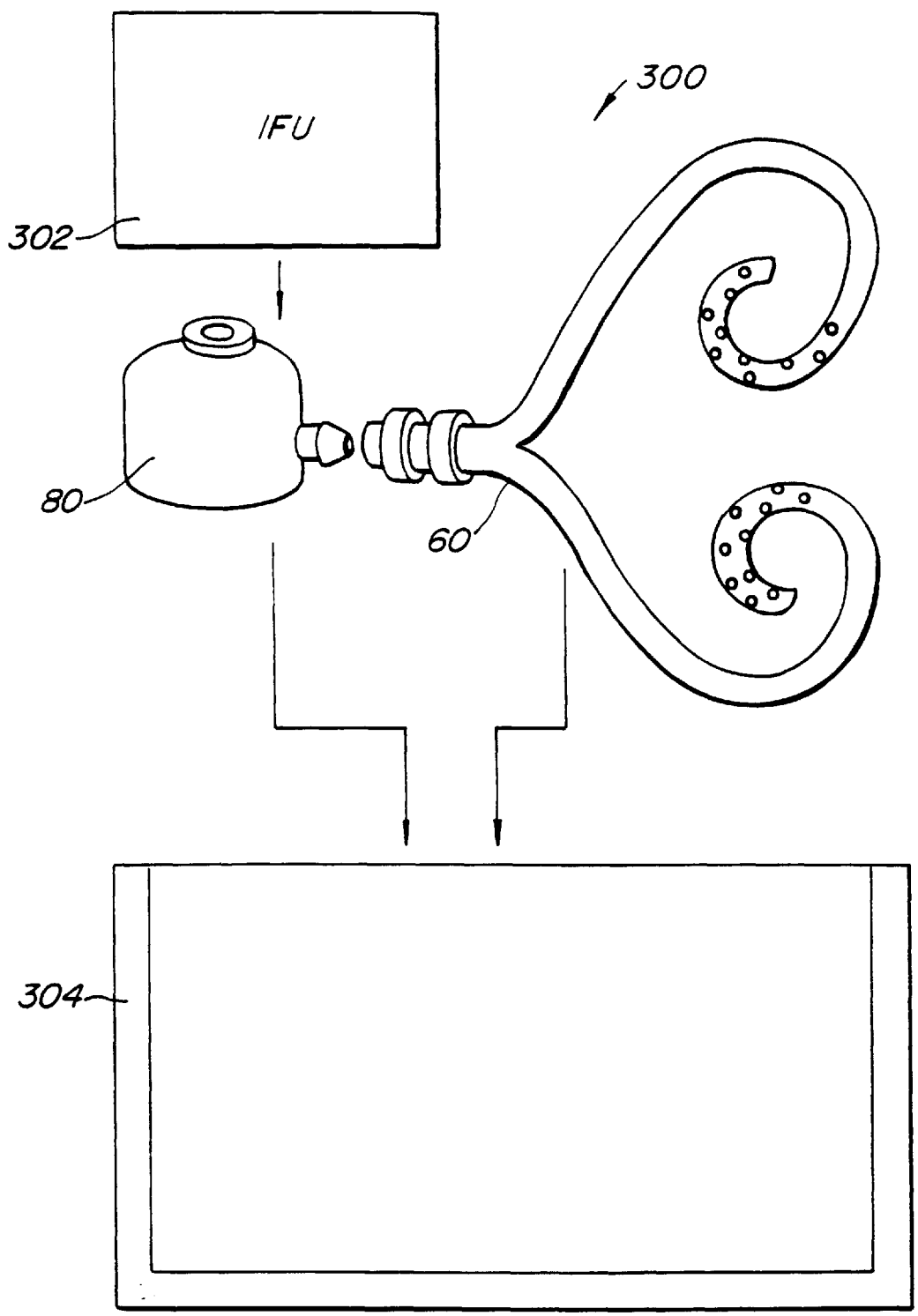
FIG. 6 illustrates a kit for implanting a peritoneal dialysis system for performing continuously cycling peritoneal dialysis according to the present invention.

Referring now to FIG. 6, a kit 300 for implanting a continuously cycling peritoneal dialysis system will be described. The kit 300 comprises at least a catheter 60 or a port 80, usually comprises both the catheter and the port together with instructions for use 302 setting forth implantation techniques and any of the continuously cycling methods described above. Usually, the kit will also include a package 304 for containing all kit components, preferably in a sterile manner. The package 304 may be a pouch, box, tube, tray, or the like. The instructions for use 302 will usually be printed on a separate sheet of paper, but optionally could be printed in whole or in part on the packaging materials.

Figure 7:
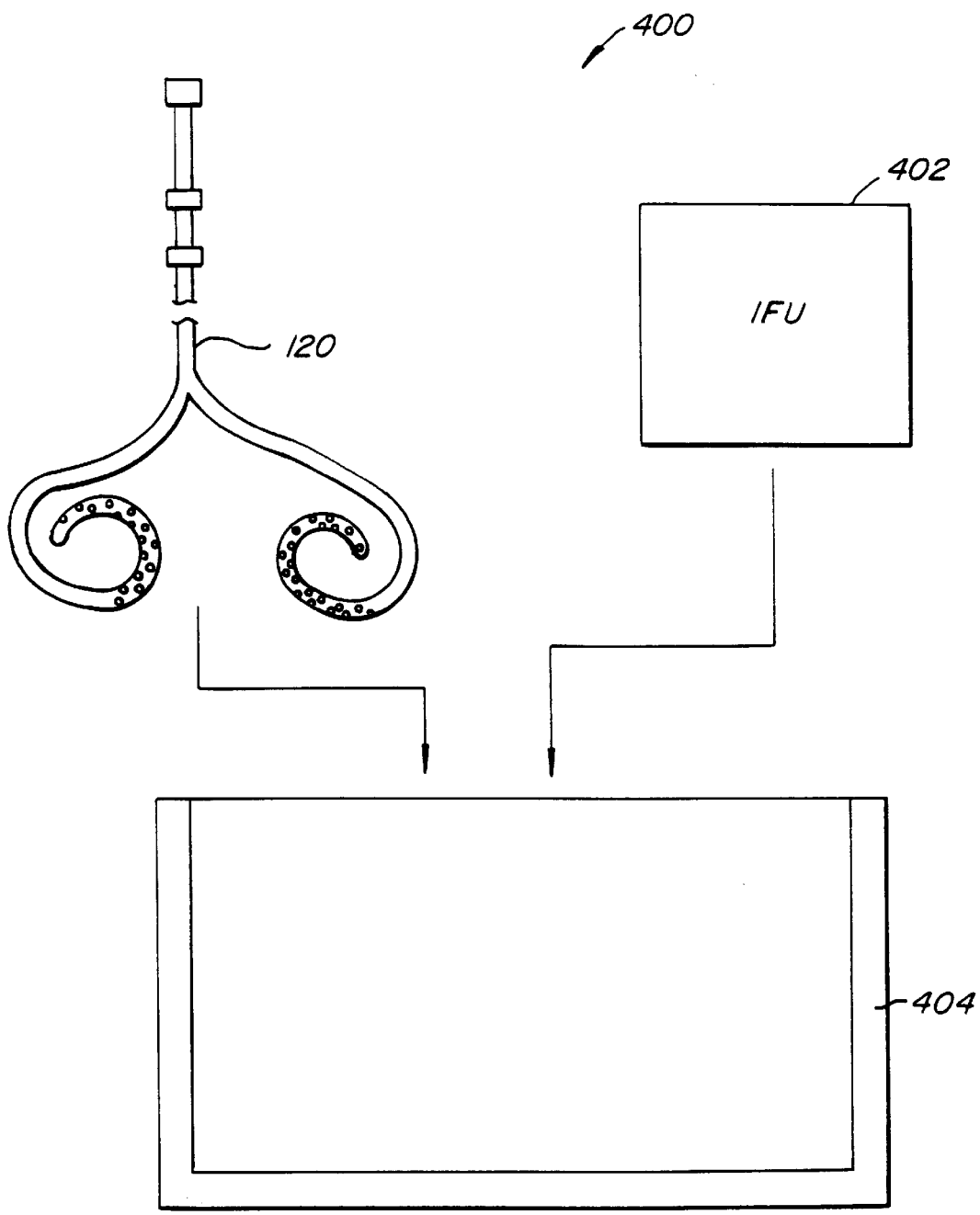
FIG. 7 illustrates a kit including the transcutaneously implantable catheter of FIG. 4.

A kit 400 for implanting the transcutaneous peritoneal dialysis catheter 120 (FIG. 5) is illustrated in FIG. 7. The kit comprises the catheter 120 as well as instructions for implantation and use 402 and usually packaging material 404. The instructions for use 402 will set forth a method for transcutaneously implanting the catheter 120 and usually methods for its use thereafter for performing continuously cycling peritoneal dialysis. The packaging 404 may have any of the configurations described above.

Figure 8:
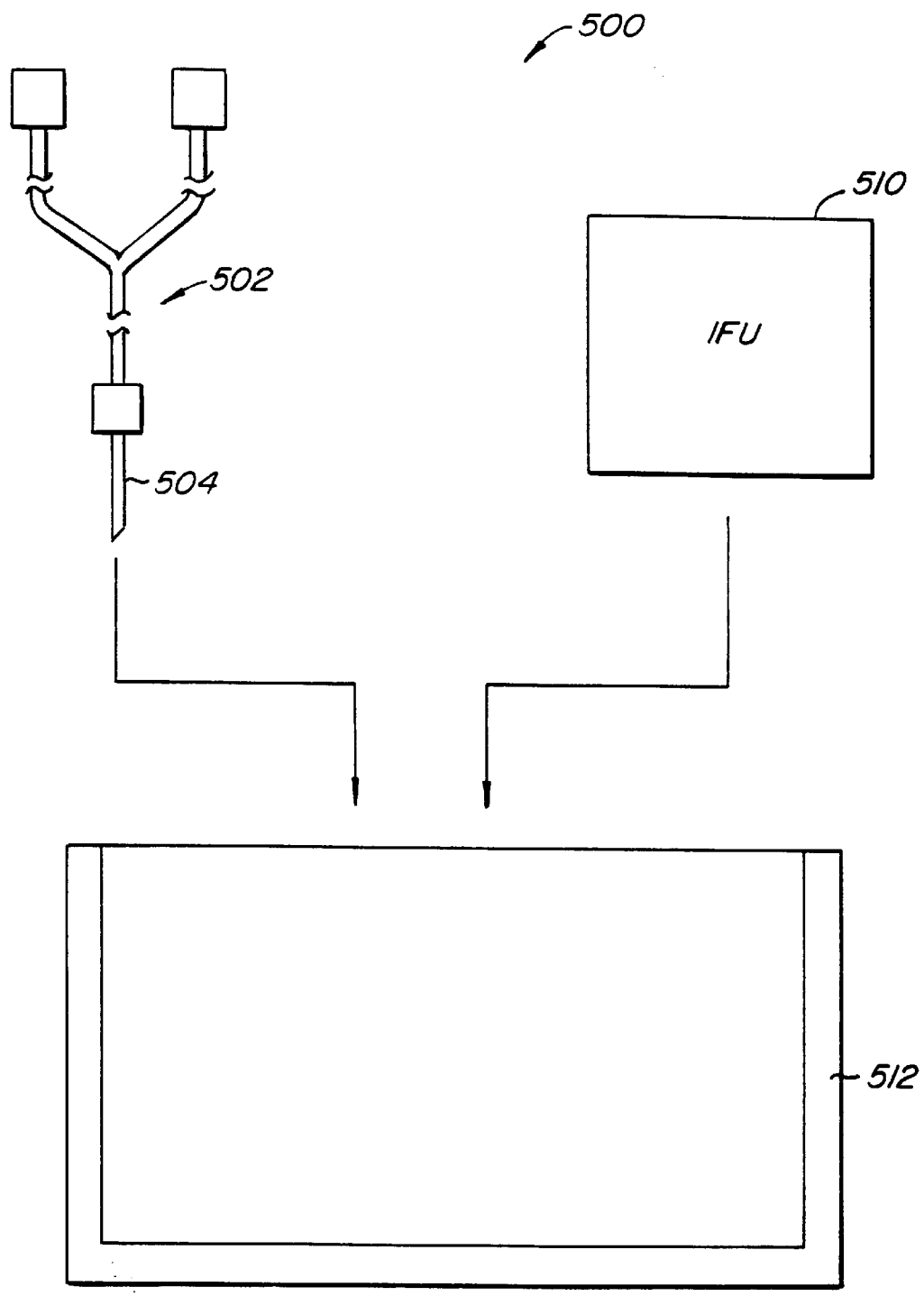
FIG. 8 illustrates a kit for performing continuously cycling peritoneal dialysis according to the present invention.

Referring now to FIG. 8, a kit 500 for performing continuously cycling peritoneal dialysis using either the fully implanted or transcutaneously implanted catheters will be described. The kit 500 will comprise at least a catheter set 502 for connecting a dialysate bag and a dialysate collection receptacle to the implanted port 80 and/or the external connection hub 128. The catheter set 502 is shown as a Y-set having an access tube 504 at one end thereof. A variety of other catheter configurations could also be provided. Additionally, pumps and other automatic control means could be provided for performing the continuously cycling treatment protocols described above. In all cases, the kits 500 will include instructions for use 510 which set forth methods for using the single access location continuously cycling peritoneal dialysis systems described above. The catheter set 502 and instructions for use will usually be packaged together in a conventional medical device package 512, e.g., a pouch, tray, box, tube, or the like. The instructions for use will usually be printed on separate paper, but optionally could be printed in whole or in part on the packaging 512.

Figure 9:
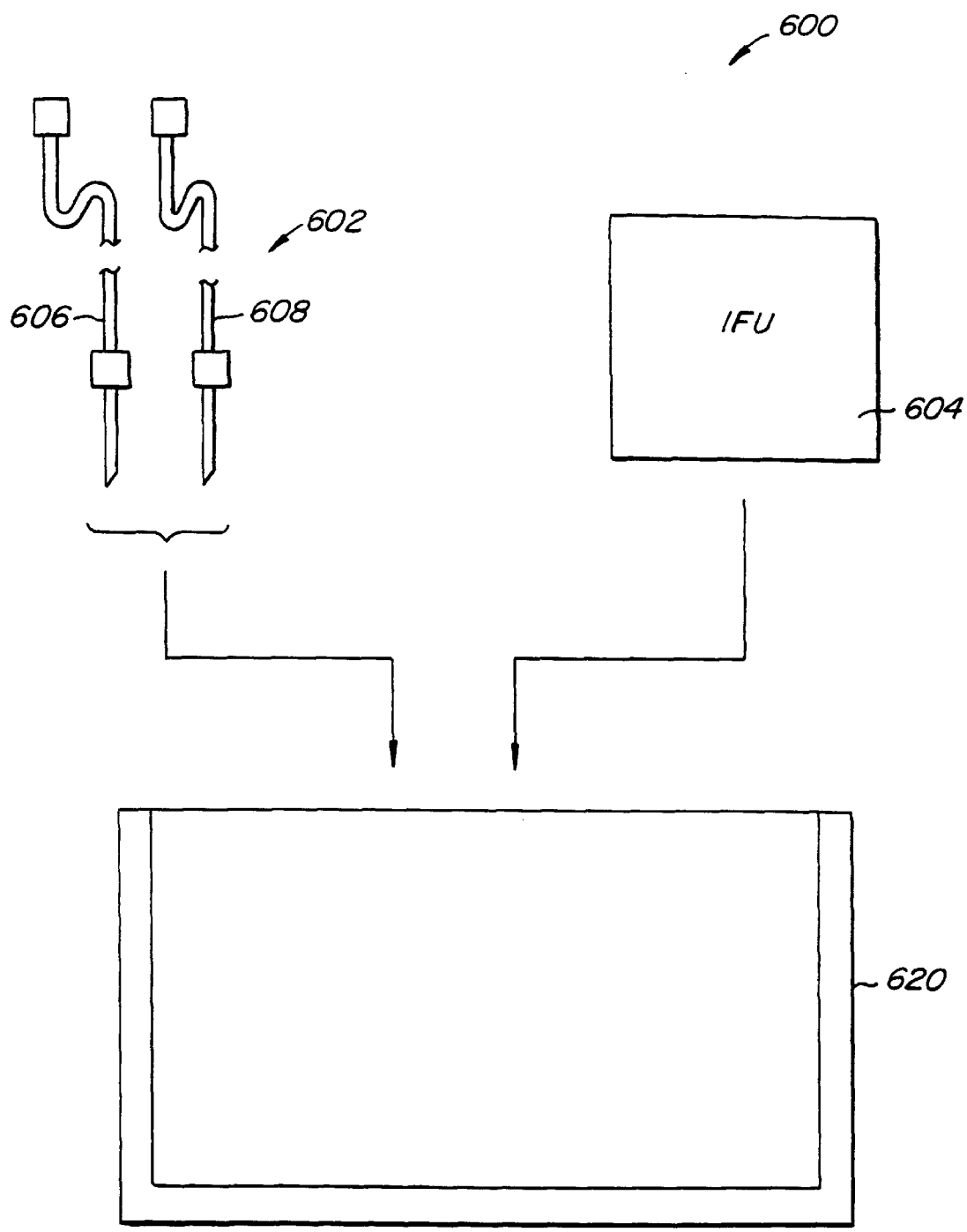
FIG. 9 illustrates a kit for performing flow-through dialysis according to the present invention.

A kit 600 for performing flow-through dialysis according to the present invention is illustrated in FIG. 9. The kit includes at least a catheter set 602 and instructions for use 604. As illustrated, the catheter set 602 comprises a pair of catheters 606 and 608 which are adapted for percutaneously accessing the implanted ports 206 and 212, as shown in FIG. 5. The catheter will be connectable to a dialysate source as well as a spent dialysate receptacle, both of which components could also be provided as part of the kit. The instructions for use 604 will set forth the method for flow-through dialysis described above. The catheter set 602 and instructions for use 604 will typically be packaged together in a pouch, tray, box, tube, or other conventional medical package 620. The instructions for use will typically be printed on a separate piece of paper, but could also be printed in whole or in part on the packaging 620.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A peritoneal dialysis catheter comprising:
    a bi-directional flow segment having a proximal end adapted to receive and discharge dialysate and a distal end;
    an infusion arm connected to receive dialysate from the distal end of the bi-directional flow segment, wherein said infusion arm is adapted to infuse dialysate into the peritoneum along its length and inhibits backflow to the bi-directional flow segment; and
    a drain arm connected to discharge dialysate to the distal end of the bi-directional flow segment, wherein said drain arm is adapted to receive dialysate from the peritoneum along its length and inhibits backflow from the bi-directional flow segment.

2. A peritoneal dialysis catheter as in claim 1, wherein the proximal end of the bi-directional flow segment is adapted for connection to an implantable port.

3. A peritoneal dialysis catheter as in claim 2, wherein the proximal end of the bi-directional flow segment is adapted for transcutaneous implantation.

4. A peritoneal dialysis catheter as in claim 3, further comprising at least one cuff circumscribing the bi-directional flow segment.

5. A peritoneal dialysis catheter as in claim 1, wherein the infusion arm comprises a valve structure which permits flow from the bi-directional flow segment to distal portions of the infusion arm and which inhibits backflow from said distal portions to said bi-directional flow segment.

6. A peritoneal dialysis catheter as in claim 1, wherein the drain arm comprises a valve structure which permits flow from distal portions of the drain arm to the bi-directional flow segment and which inhibits backflow from said bi-directional flow segment to said distal portions.

7. A peritoneal dialysis catheter 2, wherein the bi-directional flow segment the infusion arm, and the drain arm are formed as a continuous structure.

8. A peritoneal dialysis system comprising:
    a peritoneal dialysis catheter as in claim 1; and
    an implantable port adapted to be connected to the proximal end of the bi-directional flow segment.

9. A peritoneal dialysis system as in claim 8, wherein the implantable port comprises an internal valve which is opened and closed by percutaneous insertion of an access tube.

10. A peritoneal dialysis system as in claim 8, wherein the implantable port comprises a needle-penetrable membrane.

11. A peritoneal dialysis catheter as in claim 1, wherein the infusion arm and the drain arm have perforations distributed over their lengths to allow the flow of dialysate therethrough.

12. A peritoneal dialysis catheter constructed and arranged for coupling to an access device, said catheter comprising:
    an infusion arm including an inlet valve permitting liquid flow away from the access device and not toward the access device, wherein said infusion arm infuses dialysate into the peritoneum along a perforated length at the infusion arm downstream from the inlet valve; and
    a drain arm including an outlet valve permitting liquid flow toward the access device and not away from the access device wherein said drain arm receives dialysate from the peritoneum along a perforated length of the drain and upstream from the outlet valve.

13. A peritoneal dialysis catheter as in claim 12, wherein the infusion arm and the drain arm have perforations distributed over their entire lengths to allow the flow of dialysate therethrough.

14. A device for accessing a body cavity comprising:
    a housing defining a flow passage;
    an infusion arm connectable to the flow path and including an inlet valve permitting liquid flow toward the body cavity and not from the body cavity, wherein said infusion arm infuses dialysate into the peritoneum along a perforated length; and
    a drain arm connectable to the flow path and including an outlet valve permitting liquid flow from the body cavity and not toward the body cavity wherein said drain arm receives dialysate from the peritoneum along a perforated length of the infusion and downstream from the inlet valve.

15. A device as in claim 14, wherein the infusion arm has perforations distributed over its entire length to allow the flow of dialysate therethrough.

16. A device for accessing a peritoneal cavity comprising:

a housing defining a flow passage leading to the peritoneal cavity;

an infusion arm communicating with the flow passage and including an inlet valve permitting liquid flow toward the peritoneal cavity and not from the peritoneal cavity, wherein said infusion arm infuses dialysate into the peritoneum along a perforated length of the infusion and downstream from the inlet valve;

a drain arm communicating with the flow passage and including an outlet valve permitting liquid flow from the peritoneal cavity and not toward the peritoneal cavity wherein said drain receives dialysate from the peritoneum along a perforated length of the drain arm upstream from the outlet valve.

17. A device as in claim 16, wherein the infusion arm has perforations distributed over its entire length to allow the flow of dialysate therethrough.

* * * * *